US00PP17265P3

(12) United States Plant Patent
Abrams

(10) Patent No.: US PP17,265 P3
(45) Date of Patent: Dec. 12, 2006

(54) *GERANIUM* PLANT NAMED HOPE

(50) Latin Name: *Pelargonium×hortorum*
Varietal Denomination: Hope

(75) Inventor: Laura B Abrams, Sudbury, MA (US)

(73) Assignee: J P Bartlett Co., Inc., Sudbury, MA (US)

( * ) Notice: Subject to any disclaimer, the term of this patent is extended or adjusted under 35 U.S.C. 154(b) by 136 days.

(21) Appl. No.: 10/950,314

(22) Filed: Sep. 27, 2004

(65) Prior Publication Data

US 2006/0070158 P1 Mar. 30, 2006

(51) Int. Cl.
*A01H 5/00* (2006.01)

(52) U.S. Cl. ..... Plt./329

(58) Field of Classification Search ..... Plt./329, Plt./330

See application file for complete search history.

*Primary Examiner*—Wendy Haas

(57) ABSTRACT

This invention is a new and distinct cultivar of a zonal *geranium* (*Pelargonium×hortorum*) named 'Hope' the cultivar has a large dark purple blossom and darker green foliage with a medium dark zone on a stable, full, well branched plant.

1 Drawing Sheet

DESCRIPTION

Botanical designation: *Pelargonium×hortorum.*
Variety denomination: 'Hope'.

BACKGROUND OF THE INVENTION

The cultivar was developed from a controlled breeding program conducted at the J. P. Bartlett Company. The company used a non-patented cultivar designated 'Beky' (#97088) as the male parent and a non-patented cultivar designated #96033 as the female parent in a cultivated area to create a single plant 'Hope'. 'Hope's' plant habit is symmetrical with excellent basal branching. The new cultivar 'Hope' differs from its male parent in color shade being darker and vibrant. The new cultivar 'Hope' differs from its female parent in number of petals being more than its parent. The new cultivar 'Hope' is close in color to Springfield Violet. Asexual propagation of the new cultivar by cuttings at the location previously stated has shown that the unique features of this new *geranium* are stable and that the plant reproduces true to type in successive generations of asexual propagation.

SUMMARY OF THE INVENTION

The plants growth habit is compact to medium in vigor. It is a full plant that performs well in both a greenhouse and in a natural environment such as a garden. It will grow more compact under drier conditions but has the ability to be a larger and more vigorous plant with sufficient water and partial shade. The blossoms are tolerant to rain, not turning brown and rotting after a day or so of straight rain. Hope buds very early and is consistent with a fuller and rounder lasting blossom than many other cultivars known to inventor.

On average, the plant itself can get to over 210 millimeters tall, not including the stem or flower. The free branching nature of Hope allows the plants girth to grow and flourish. The width of a single plant is measured to be 291 millimeters and growing. The vibrancy of blossom color and strong green leaf color separates itself from any other known to inventor. The double blossom is a dark purple. 'Hope's' stem is a distinguished medium green, while the leaf produces a medium darker zoning. 'Hope's' standout performance is regarded highly due to its excellent growth habit, size, blossom and leaf. The new cultivar of the present invention is being marketed under the BARTLETT'S trademark.

BRIEF DESCRIPTION OF THE PHOTOGRAPH

Accompanying this application is a photographed picture of the plant and its' aspects.

Figure 1:
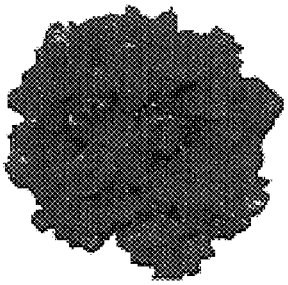

1. FIG. 1 shows the large, double blossom and the purple color described in the summary.

Figure 2:
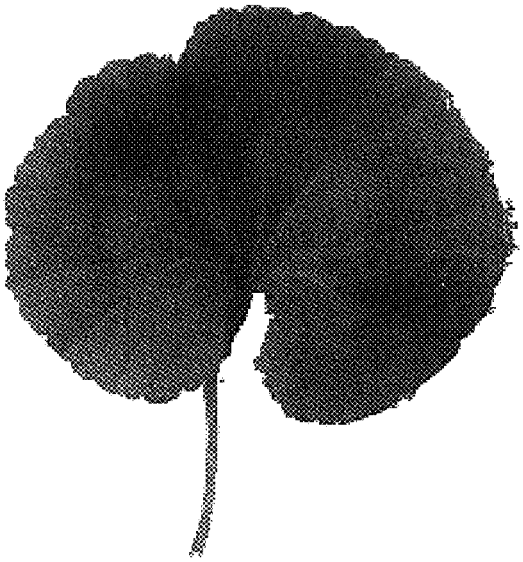

2. FIG. 2 enables us to see the darker green leaf with the medium green zone.

Figure 3:
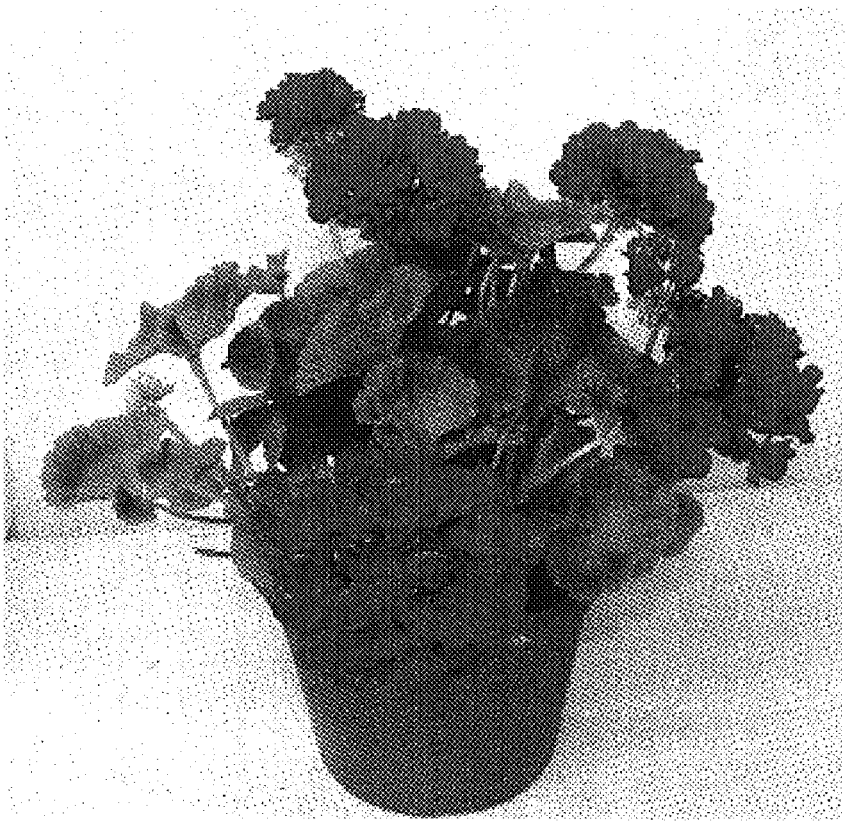

3. FIG. 3 shows the overall plant. This is a single plant from a cutting in a four-inch pot. The height, width, and growth habit are clearly seen here.

DETAILED BOTANICAL DESCRIPTION

The following observations and measurements describe asexual reproductions of 'Hope' grown in greenhouses located in Sudbury, Mass., USA. The plant history was taken on 3 month old plants grown in 7.5" pots, blossomed under natural light in a greenhouse and color readings were taken in the greenhouse in Sudbury, Mass. under ambient light. Color references are primarily to the Pantone Color Selector Chart 1000/coated 1995. The color values were determined on May 11, 2004 under natural light conditions of 200 foot-candles.

Classification:
*Botanical.*—*Pelargonium×hortorum* cv. 'Hope'.
Inflorescence:
A. Umbel:
*Flowering duration.*—The flowers last approximately 13 to 18 days under standard greenhouse conditions and then dehisce.

*Average diameter.*—Approximately 8.7 to 9.3 cm.
*Average depth.*—Approximately 7.5 to 8.2 cm.
*Peduncle length.*—Approximately 1.6 to 2.4 cm.
*Peduncle diameter.*—Approximately 0.4 to 0.5 cm.
*Pedicel length.*—Approximately 2.5 to 3 cm.
*Number of umbels per plant.*—When grown in a 7.5" pot at 8 weeks after the sticking of a rooted cutting, there commonly is approximately 5 to 7 umbels per plant. The umbels form approximately 6 to 10 cm above the foliage.
*Number of florets/umbel.*—When grown in a 7.5" pot at 8 weeks, approximately 29 to 34 florets per umbel commonly are formed.
*Flower depth.*—Approximately 6.5 to 7.5 cm.

B. Corolla:
*Buds.*—Elliptical to round in configuration, initially light green and changing to dark purple at the time of opening, and approximately 11 to 14 mm. in length and approximately 6 to 8 mm. in width.
*Pedicels.*—Commonly approximately 4 to 5.5 cm in length and straight which commonly causes a full round blossom when all buds open.
*Average diameter.*—Approximately 6 to 7 cm.
*Form.*—Commonly double with at least three petaloids.
*Petals.*—Spatulate shaped, satiny and smooth. Commonly approximately 15 to 17 petals are present per floret. Petal base is V-shaped with a semi-circular margin. Petal length is approximately 1.5 cm and the diameter is approximately 0.7 cm. Upper petal surface is smooth opposed to lower petal surface being slightly rougher.
*Number of petaloids.*—Commonly forms approximately 3 to 4 petaloids per floret. The petaloids are exactly the same as the petals excepting their diameter are approximately 0.4 cm.
*Color.*—General tonality surface from a distance of three meters: Dark Purple.
*Color of upper petals.*—Pantone 2405C.
*Color of lower petals.*—Pantone 240C.
*Markings of upper petals.*—None.
*Sepals.*—7 to 10 sepals per floret with a length of approximately 0.3 to 0.7 cm and width of 0.04 to 0.08 cm. The overall shape is elliptical with a V-shaped base and margin and semi-circular apex. Upper and lower surface are the same texture and color. Smooth, non-glossy with both Pantone 367C.

C. Reproductive organs:
*Androecium.*—5 fertile anthers, with whitish filaments, orange pollen the lower side of the mature (open) anther. The surface of the anther under the pollen is black.
*Gynoecium.*—5 lobed purple stigma, Pantone 2425C, greenish style, Pantone 377C; one pistil, Pantone 367C per flower.
*Fertility/seed set.*—Commonly does not produce fruits in the absence of mechanical fertilization.
*Spring flowering response period.*—Approximately 5 to 8 weeks from rooted cuttings under standard greenhouse conditions.
*Outdoor flower production.*—Freely flowering under outdoor growing conditions with substantially continuous blooming.
*Durability.*—Ships well.
*Pest/disease resistance/susceptibility.*—No susceptibility to pests or diseases noted to date. Disease resistance has not been tested to date.

Plant:

A. Foliage: Medium Dark green with medium dark zonation. Zoning color is Pantone 350C. The leaves are pubescent on the upper surface, and smooth on the lower surface.
*Length.*—2.25 to 2.75 cm.
*Width.*—2.75 to 3.25 cm.
*Form.*—Reniform, with a cordate base.
*Margin.*—Irregularly crenate.
*Ribs and veins.*—Palmate 2.25 to 2.75 cm. long.
*Leaf color.*—Upper side is Pantone 364C. Under side is Pantone 371C. Leaf upper surface covered predominately with trichome Pantone 364C and leaf surface is predominately smooth.
*Petioles.*—Commonly approximately 5 to 7 cm long with a diameter of 0.04 cm to 0.08 cm.
*Petiole color.*—Pantone 367C.

A. General appearance and form:
*Internode length.*—Commonly varies from approximately 0.9 to 1.1 cm.
*Branching pattern.*—Freely basal branching as well as lateral branching. No pinching is required to obtain self-branching. A self-branching growth habit is observed in the absence of a growth regulator.
*Height.*—Approximately 22 to 24 cm. above a 7.5" pot at 8 weeks under standard greenhouse conditions.

It is claimed:

1. A new and distinct variety of *geranium* plant herein illustrated and described.

* * * * *